United States Patent [19]
Zeffren et al.

[11] 3,935,868
[45] Feb. 3, 1976

[54] HAIR SETTING PROCESS

[75] Inventors: Eugene Zeffren, Wyoming; Jerry Turner, Fairfield, both of Ohio

[73] Assignee: The Procter & Gamble Company, Cincinnati, Ohio

[22] Filed: Feb. 1, 1974

[21] Appl. No.: 438,816

Related U.S. Application Data

[62] Division of Ser. No. 294,053, Oct. 2, 1972, Pat. No. 3,805,809.

[52] U.S. Cl............................... 132/7; 424/71
[51] Int. Cl.² ................................... A45D 7/00
[58] Field of Search ........ 132/7; 424/71; 260/243 R

[56] References Cited

UNITED STATES PATENTS

| | | | |
|---|---|---|---|
| 2,774,355 | 12/1956 | Bell | 132/7 |
| 2,865,811 | 12/1958 | Ruesch | 424/71 |
| 3,266,994 | 8/1966 | Reiss | 424/71 |

*Primary Examiner*—G. E. McNeill
*Attorney, Agent, or Firm*—Douglas C. Mohl; J. D. Schaeffer; Richard C. Witte

[57] ABSTRACT

A process for deforming hair by applying thereto a solution containing a monopersulfate salt of the formula $MHSO_5$, wherein M is an alkali metal cation.

4 Claims, No Drawings

HAIR SETTING PROCESS

This is a division of application Ser. No. 294,053, filed Oct. 2, 1972, now U.S. Pat. No. 3,805,809.

BACKGROUND OF THE INVENTION

This invention relates to a process for deforming hair. More particularly, the invention discloses processes and compositions for curling or straightening human hair employing monopersulfate oxidizing agents which do not substantially bleach melanin when employed under the conditions hereinafter disclosed.

Both hot and cold hair curling processes involve various heat or chemical treatments, or combinations thereof, to disrupt the keratin structure of the hair. Following this initial disruption, the hair is subjected to longitudinal stresses, for example, by winding on a mandrel, following which the keratin structure is substantially reestablished with the hair in the curled configuration. Curling processes employing heat and caustic solutions are known as "hot" processes, whereas those employing chemical compounds such as the thioglycolates are known as "cold" processes. Cold processes have come into general acceptance inasmuch as they can be utilized by relatively inexperienced operators in home permanents.

It is recognized in the art that hair which has been extensively bleached, i.e., subjected to oxidative conditions whereby the malanin is substantially destroyed, is relatively easy to curl or set in a more-or-less permanent configuration by simply moistening the hair and subjecting it to a longitudinal stress. Presumably, common hair bleaches disrupt chemical bonds in keratin fibers with a net effect similar to that when hair is contacted with a thioglycolate cold waving solution. Hair in which the keratin molecules are oxidatively disrupted is thereby rendered deformable and the hair can then either be curled or straightened, as desired. Of course, hair treated with the common hair bleaches, e.g., a basic solution of hydrogen peroxide, is not only more susceptible to curling but also has a different color due to the action of the bleach on the malanin color bodies in the hair. For this reason oxidative hair bleaches are not generally considered to be acceptable for curling hair inasmuch as the user must thereafter tint or dye the treated hair to reestablish the original hair color.

It has now been discovered that a certain class of oxidizing agents, the monopersulfates, can be applied to hair to oxidize the chemical bonds in keratin, thereby rendering the hair deformable without substantial bleaching of the natural hair color. It is surprising that the monopersulfates are capable of disrupting the keratin fibers without attendant bleaching, inasmuch as these compounds are well-known as bleaches for synthetic fibers. Presumably, the kinds of stains which can be bleached from fabrics and fibers are sufficiently different from the melanin coloration of the hair that the monopersulfates, while capable of bleaching such stains, have no substantial effect on malanin. In any event, it has now been found that monopersulfates can be applied to hair to cause sufficient disruption of the keratin fibers to allow the deformation of the hair by applying a longitudinal stress thereto, but without changing the natural hair color.

The use of per-salts, including persulfates and monopersulfates in the neutralizing solution of hair waving compositions is known in the art; see, for example, U.S. Pat. No. 3,583,408 and ELCHEM 1384 Catalog, DuPont. When employed as neutralizers, such per-salts are commonly used in the acid pH range following the thioglycolate treatment to reestablish the sulfur-sulfur bonds in the keratin fiber, whereas by the present process it has been discovered that monopersulfates can be employed to disrupt keratin bonds. U.S. Pat. No. 3,679,347 teaches the use of monopersulfates in hair dyeing processes, but does not suggest their use for deforming hair in the manner of this invention.

The concurrently filed application of J. A. Anderson, entitled "Hair Setting Process", Ser. No. 294,052, filed 10/2/72 now U.S. Pat. No. 3,809,098, discloses hair curling processes employing monopersulfates and certain chelating agents.

It is an object of the present invention to provide a method for deforming keratin fibers, especially human hair, by means of monopersulfate oxidizing agents without substantial hair bleaching.

It is a further object herein to provide a method for curling hair by means of monopersulfate oxidants. These and other objects are obtained herein as will be seen by the following disclosure.

SUMMARY OF THE INVENTION

The instant invention encompasses a process for deforming hair comprising contacting said hair with an effective amount, i.e., an amount sufficient to thoroughly wet the hair, of an aqueous solution comprising from about 1% to about 20% by weight of an oxidant of the formula $MHSO_5$ wherein M is an alkali metal cation, the pH of said treatment solution being in the range from about 5 to about 11. The hair is treated with the solution of the $MHSO_5$ oxidant for a period from about 1 to about 30 minutes, following which the oxidant is removed by a water rinse or shampoo; the moist, treated hair is subjected to a longitudinal stress to achieve any desired configuration. For example, the wet hair can be wound on a mandrel and allowed to dry on the mandrel, thereby achieving a curled effect. Alternatively, the wet hair can be fashioned into a straight configuration and allowed to dry, thereby resulting in hair straightening. In an alternate mode, the hair can be subjected to a longitudinal stress during treatment with the oxidant, rinsed, and allowed to dry in the stressed configuration. Again, curling or straightening, as desired, is thereby obtained.

DETAILED DESCRIPTION OF THE INVENTION

The oxidizing agents used in the present process are watersoluble monopersulfate salts of the formula $MHSO_5$, wherein M is an alkali metal cation, i.e., lithium, sodium, potassium, rubidium or cesium. The nature of the alkali metal cation is of no import to the present invention inasmuch as all such salts are watersoluble and it is the monopersulfate anion which is the active oxidizing species in solution. However, the monopersulfate salts wherein M is potassium are available from E. I. DuPont de Nemours Co. under the trade name OXONE and are preferred herein because of this commercial availability. The other alkali metal monopersulfate salts can be prepared, for example, by ion exchange reactions with the potassium salt or by neutralization of the corresponding acid with the appropriate alkali metal hydroxide.

The foregoing monopersulfate salts are employed in the present process as aqueous solutions containing from about 1% to about 20%, preferably 2% to about 10%, by weight of said monopersulfate salt. The pH of the aqueous monopersulfate solutions used herein is adjusted to within the range from about 5 to about 11. Solution pH's greater than 11 can be used; however, such high pH's are unduly irritating to normal skin and are preferably avoided. A solution pH of about 7.0–9.5 is preferred. Solution pH's within the desired range can be established by dissolving the monopersulfate salt in water and adding sufficient base, e.g., alkali metal hydroxide, ammonium hydroxide, or organic base such as diethanolamine, triethanolamine and the like, to the solution until the desired pH within the specified range is obtained. However, it has been discovered that the pH of such solutions normally will change to the acid range when applied to the hair. Accordingly, it is preferred that a buffer be employed in the aqueous solution of monopersulfate to keep the pH within the range of about 5 to about 11. Any of the common organic and inorganic buffer salt combinations capable of establishing a pH within this range are suitable for use in conjunction with the monopersulfate salts. Exemplary buffers suitable for use herein include, for example, the sodium hydroxide + sodium borate; sodium hydrogen phosphate + potassium dihydrogen phosphate; sodium borate + hydrochloric acid; and phosphate buffers prepared in the manner fully described in "Hawks Physiological Chemistry", Oser, Ed. 14, pps. 41–43, McGraw-Hill (1965).

As noted hereinabove, it is necessary that the monopersulfate salt in contact with the hair be maintained at a pH in a range from about 5 to about 11 to provide the desired hair deformation. While any of the common buffers suitable for use in this pH range can be employed for this purpose, it has been discovered that carbonate-bicarbonate buffers are most preferred herein. Presumably, carbonate-bicarbonate buffer mixtures employed in conjection with the alkali metal monopersulfates serve both as a pH buffer and, in some way, promote the softening of the hair or otherwise allow the monopersulfate to interact with the keratin in an optimal fashion. Irrespective of the actual mechanism, it has been found that compositions employing the monopersulfate salt dissolved in aqueous carbonate-bicarbonate buffers at a pH in the range from 5 to 11, preferably 7.0–9.5, are preferred for use herein. Accordingly, aqueous solutions comprising from about 1% to about 20% by weight of the alkali metal monopersulfate, preferably $KHSO_5$, from about 0.5% to about 10% by weight of sodium bicarbonate and from about 0.5% to about 10% by weight of sodium carbonate, the balance of said compositions comprising water, are preferred for use herein to deform hair. The total concentration of mixed carbonate-bicarbonate buffer in such compositions is preferably from about 5% to about 15% by weight.

Aqueous solutions of the monopersulfate salts used herein decompose when stored for periods in excess of about 24 hours. As noted hereinabove, it is necessary to the practice of this invention that the solutions contain not less than 1% by weight of the $MHSO_5$ salt. Of course, highly concentrated solutions of $MHSO_5$ salts can be prepared which can be stored for several weeks or months without decomposing below the 1% limit. However, this is economically wasteful and it is preferable to use freshly prepared $MHSO_5$ solutions herein. In the present connotation, a "freshly prepared" solution is an aqueous solution of the monopersulfate salt which is prepared within about one-half hour prior to application to the hair.

The monopersulfate solutions herein can contain additional components which serve to aid in their application to hair. For example, various gelling agents such as silica gel, high molecular weight polyoxyethylenes, carboxymethylcellulose, veegum, and the like can be used in such solutions as thickeners for the convenience of the user. Various surfactants, for example the alkylbenzene sulfates and sulfonates and nonionic surfactants, such as polyoxyethylene condensates of alkyl phenols, as well as sodium and potassium soaps, can be present in the compositions to improve rinseability thereof, thereby aiding in removal from the hair once the treatment is complete. Various perfumes, emollients, conditioning aids such as silicone derivatives and the like can be present in the compositions to provide pleasing cosmetic and aesthetic aspects thereto. It is to be understood that all manner of such nonionic, anionic and amphoteric auxiliary materials commonly used to enhance the cosmetic aspect of hair curling compositions can be employed in the present compositions provided that such selected materials are stable and compatible with the monopersulfates at the intended pH use range herein. However, hydrocarbyl quaternary ammonium salts materials commonly employed in hair softening compositions interfere with the action of the monopersulfates on hair and, hence, are preferably avoided in the compositions and processes herein.

The instant process of deforming hair, i.e., curling or straightening, can be carried out over a temperature range of from about 0°F. to about 150°F. Of course, use of the higher temperatures within the range, for example, by means of a hair dryer or electrically heated hair curler, will increase the rate of curling. Use of colder temperatures within the range will reduce the rate. Curling processes are generally carried out at a room temperature of from about 65°F. to about 90°F., and this temperature range is preferred in the instant process.

In the process of curling hair by applying a solution of a monopersulfate salt, a longitudinal stress is applied to the hair to achieve deformation and the desired hair set. The hair to be curled is wound on a mandrel and held in place during the curling operation. The types of mandrels used for this purpose are those well known in the art, including the spiral rod and the Croquignole curler. When the spiral rod mandrel is employed, the hair on the head is divided into multiple sections, usually four to about eight. The sections are then subdivided into smaller squares, ca. 1 in. × 1 in. Starting at the proximal end, the hair in each block is then wound on the mandrel in the shape of a helix. The distal ends are held by a string, or clip, or other holding device.

When the Croquignole curler is employed to curl hair, the process is somewhat different. The hair on the head is sectioned into blocks ranging in size from about ½ to 1 inch × 2 to 3 inches, depending on the final hair style envisioned. The hair in each block is then combed and the distal ends are placed centrally on the mandrel, which is then wound and secured in place by means of a rubber band or other clipping device. In both the spiral rod and Croquignole techniques, end papers can be used to facilitate collecting the distal ends.

In still a third technique, which results in the formation of relatively large, loose curles, the hair is wound in a generally circular configuration without special winding devices and set into place by means of hair pins or clips. These so-called pin curls have a very large diameter and result in a very loose set. By proper selection of the means whereby the longitudinal stress is applied to the hair, curls of varying degrees of tightness can be achieved. Spiral winding results in the formation of relatively tight curls; Croquignole winding yields somewhat looser curls; while pin curls are usually quite loose.

In one method of curling hair by means of a solution of a monopersulfate salt, the hair is first wound as described above, depending on the type of curl desired. The winding can be done with dry hair, moistened hair or hair moistened with the solution of monopersulfate salt. Preferably, the hair is shampooed, rinsed and towel dried prior to winding. After winding, the hair is thoroughly saturated with the monopersulfate solution. Additional monopersulfate solution can be applied from time-to-time during the curling step to keept the hair thoroughly saturated. The solution is allowed to remain in place from about 1 minute to about 30 minutes, depending on the strength of the monopersulfate solution and the degree of curl tightness desired. The treatment time will also depend to a certain extent on the coarseness of the hair, coarser hair requiring longer times within the range noted to achieve a curl. Likewise, longer times within the range are usually required when children's hair is being curled by this process. If hair has been rendered porous by peroxide bleaching or by sun or weather damage, a shorter time in the range is sufficient to impart the desired curl. The time necessary to achieve a curl can be determined by the user prior to application to the head by means of a test curl. Generally, coarse thick hair will require a curling time of about 30 minutes when a 2% solution of the monopersulfate salt is employed. Damaged hair will require from about 1 to about 10 minutes to achieve a curl when a 2% monopersulfate solution is employed; children's hair will require from about 20 to about 30 minutes to achieve a curl under the same conditions. For most purposes, it is preferable that the solution of monopersulfate remain in contact with the hair for a period of time from about 5 minutes to about 15 minutes.

In a preferred process herein, the hair to be curled is contacted with an aqueous solution of the monopersulfate oxidant under the conditions of pH, time and temperature as noted hereinabove, while said hair remains in its natural configuration. Following treatment with the monopersulfate oxidant solution, the solution is removed from contact with the hair by a water rinse or by shampooing. The hair is then moistened with water and subjected to a longitudinal stress, e.g., by winding on a mandrel if the hair is to be curled, or by brushing if the hair is to be straightened. The hair is then allowed to dry while in the stressed configuration. It is to be recognized that this procedure is suitable for resetting or re-curling hair which has been deformed by the reaction of a solution of the monopersulfate salt in the manner of this invention. That is to say, hair which has had its keratin structure disrupted by the monopersulfate salt can be re-curled, re-straightened or otherwise deformed, as desired, by simply moistening the hair, again subjecting it to the appropriate longitudinal stress, and allowing it to dry.

Hair can be straightened in the manner of this invention by contacting said hair with an aqueous solution of an alkali metal monopersulfate salt under the same conditions of pH, time and temperature as those used in the waving processes disclosed above. For example, the hair can be wound in a Croquignole winding using curlers having a diameter of from about 2½ inches to about 3½ inches and allowed to dry. Hair rolled on rollers of such large diameter will fall into a substantially straight configuration upon final brushing. In an alternate straightening procedure the hair is treated with the monopersulfate solution and then the wet hair is brushed into a straight configuration. The hair is then simply allowed to dry in the straightened configuration.

The foregoing processes are preferably carried out by contacting the hair with a freshly-prepared aqueous solution comprising from about 1% to about 20% by weight of $KHSO_5$, from about 0.5% to about 10% by weight of sodium bicarbonate, and from about 0.5% to about 10% by weight of sodium carbonate, for a period of time from about 1 minute to about 30 minutes; (2) rinsing the hair with water to remove substantially all of the $KHSO_5$; and (3) subjecting the moist hair to a longitudinal stress to achieve the desired configuration and (4) allowing said hair to dry in the stressed configuration. Hair treated in this manner can be remoistened with water and reset several times and a good set can be achieved each time by simply subjecting it to a longitudinal stress.

An important advantage of the instant process is that hair treated with the monopersulfate solution can be re-set several times by simply rewetting the hair, subjecting it to a stress, and allowing it to dry. In this manner, hair can be re-styled as desired by the user. However, it has been found that polyvalent metal ions, presumably calcium and magnesium ions dissolved in ordinary tap water, may have a cumulative adverse effect on the setting properties of hair which has been treated with the monopersulfate solution. That is to say, hair treated in this fashion eventually absorbs sufficient calcium and/or magnesium ion that it is no longer as capable of being set by simple treatment with water. When this occurs, the hair must again be treated with an aqueous solution of a monopersulfate salt to restore its deformable characteristics. For this reason, it is desirable herein that the water used in any of the process steps, i.e., the water used in the solutions of monopersulfate, the water used to moisten the hair prior to setting, and the water used to remove the monopersulfate from the hair, be substantially free from polyvalent metal ions. Accordingly, it is desirable that deionized water be employed in the compositions and processes herein. By so doing, hair treated with the monopersulfate salt is capable of being set and reset up to about 10 or more times without the need for additional treatments with the monopersulfate solution.

The following examples illustrate the hair deforming process of this invention but are not intended to be limiting thereof.

EXAMPLE I

Hair switches, ca. $2 \pm 0.2$ g. per switch, were soaked in a freshly prepared aqueous solution consisting of 4% by weight OXONE (commercial material comprising 41.5% $KHSO_5$, the balance being equal proportions of $K_2SO_4$ and $KHSO_4$) and 5% by weight total carbonate buffer, comprising a mixture of 0.1% by weight sodium carbonate and 4.9% by weight sodium bicarbonate. The pH of the solution was 8.0. Soaking was carried out for 30 minutes at room temperature (ca. 72°F).

Immediately following treatment with the foregoing buffered OXONE solution, the hair was shampooed with a commercial shampoo composition containing anionic surfactants and thoroughly rinsed with water. The treated hair, which had a silky-slick feel, was wound in a Croquignole fashion on a mandrel (commercial hair curler; diameter ca. ¼ in.). The hair in the wound configuration was allowed to dry at room temperature over a period of about 4 hours. Following this, the hair was removed from the mandrel. The natural hair color was not substantially changed by this treatment.

The curled hair switch obtained in the foregoing manner was tested for set retention of the curl (as measured by % curl loss) as follows. The curl was suspended in a closed chamber containing a saturated solution of ammonium chloride, which provided a constant relative humidity of about 80%. The distance the curl unwound after having been in the closed chamber for a two hour period was then measured and the percentage curl loss was computed by the following equation:

$$\% \text{ loss of curl} = \frac{\text{length of curl drop (inches in 2 hours)} \times 100}{\text{length of hair switch (inches)}}$$

Control switches set with various commercial setting gels and setting liquids, as well as with ordinary tap water, were used as controls in the test to measure the relative effect of the monopersulfate treatment. Test results are set forth in Table 1, below.

Table 1

| Hair Treatment | % Loss of Curl |
|---|---|
| 4% OXONE + 5% carbonate buffer | 12 |
| Control A[1] | 57 |
| Control B[2] | 63 |
| Tap Water Set | 55 |

[1]Commercial, non-thioglycolate hair setting gel
[2]Commercial, non-thioglycolate hair setting liquid The foregoing data clearly demonstrate that hair which has been oxidized by the monopersulfate solution will accept and retain a curl imparted thereto by a longitudinal stress to a far greater extent than does unoxidized hair set with water or with representative, commercial, non-thioglycolate hair setting preparations.

In the foregoing procedure treatment times with the monopersulfate solution of 1,5,10 and 15 minutes are employed, respectively. In each instance the curl retention of hair treated with the potassium monopersulfate solution is substantially greater than that of hair curled for an equivalent time with water or with the commercial, non-thioglycolate setting gel or setting lotion.

Hair curled in the foregoing manner is shampooed, rinsed in tap water and re-set to achieve a new hair style. This treatment is repeated about 7 times, after which the setting properties of the hair are partially lost.

The foregoing procedure is modified by using deionized water to prepare the solution of OXONE and in the water rinse. Hair thus treated can be re-wetted with deionized water and re-curled 10 times without substantial loss of its setting properties.

EXAMPLE II

Hair on a human test subject is cleaned with a commercially available shampoo containing anionic surfactants and thoroughly rinsed with water. The hair on the head is sectioned into blocks having an average area of about 3 in.² by means of a styling comb. Distal ends of the hair are collected in tissue end papers and wound in Croquignole fashion around commercial 3/8 in. curlers and affixed in place at the head with rubber coated spring clips.

The curled hair on the subject's head is then thoroughly saturated with a freshly prepared solution comprising 5% by weight $KHSO_5$, 5% by weight sodium bicarbonate, 0.8% by weight sodium carbonate, 4% by weight carboxymethylcellulose thickener, the balance of said composition comprising water. The pH of the composition is about 8.4. The curled hair saturated with the monopersulfate composition is allowed to remain in place for about 5 minutes. Following this time, each curl is again saturated with an additional quantity of the fresh monopersulfate solution and the hair is allowed to remain in place in the curlers for an additional 15 minutes. Following this second 15 minute period, the hair is removed from the curlers and thoroughly rinsed with water. The hair is then towel dried.

Hair treated in the foregoing manner is found to have a substantial curl and improved body properties over hair set in similar fashion using ordinary tap water or a commercial, non-thioglycolate setting gel. The natural hair color is not affected.

In the above process, the potassium monopersulfate is replaced by an equivalent amount of lithium monopersulfate, sodium monopersulfate, rubidium monopersulfate and cesium monopersulfate, respectively, and equivalent hair curling results are secured.

The foregoing curling process is carried out using solutions of potassium monopersulfate at pH's of 7, 9, 9.5, 10 and 11, respectively; at each pH the hair is found to be substantially deformed and curled by the process.

EXAMPLE III

A hair straightening pomade is prepared as follows. To an aqueous gel comprising 5.5 parts by weight sodium carbonate, 5 parts by weight sodium carboxymethylcellulose, 3 parts by weight magnesium aluminum silicate (veegum; binder) and 100 parts by weight water are added 25 parts by weight OXONE. The OXONE is blended into the gelatinous mixture by hand to yield a thick pomade.

The freshly prepared pomade paste prepared in the foregoing manner is applied to water-wet, naturally curly hair and rubbed in with the fingers for about 5 minutes. Following this, the hair coated with the pomade is brushed until a substantially straight configuration is achieved. The thickness of the pomade helps maintain this longitudinally stressed configuration. Following the brushing operation, the hair in its straightened configuration is coated with additional, fresh monopersulfate pomade which is then allowed to remain on the hair for a period of about 30 minutes. Following the second treatment with pomade, the hair is rinsed and thoroughly shampooed. Thereafter, the wet hair is brushed into a substantially straight configuration and allowed to dry. After drying, the hair retains the straight configuration. The natural color of the hair is not affected by this treatment.

In a modification of the above procedure, the hair coated with the monopersulfate pomade and in the substantially straight brushed configuration is heated to a temperature of about 150°F. As the pomade dries it is replaced by additional pomade, from time to time. Following about 10 minutes of the heat treatment, the hair is rinsed in water, shampooed, brushed into a substantially straight configuration and dried with an electric dryer at about 150°F. This treatment is particularly useful in straightening extremely coarse, curly hair in a relatively short period of time without modifying the natural hair color.

As noted hereinabove, the monopersulfate hair deforming compositions of this invention are preferably applied to clean hair. That is to say, hair which has had its coating of dirt and excess lipids removed by shampooing is more susceptible to oxidation by the monopersulfate solution and improved treatments are thereby secured. In a preferred embodiment of this invention, the shampoo and monopersulfate solution are applied to hair concurrently. Accordingly, shampoo compositions containing the monopersulfate oxidizing agent and having a pH from about 5 to about 11 can be prepared and applied to the hair to cleanse and oxidize said hair simultaneously. Following treatment with the monopersulfate-containing shampoo, the hair is rinsed with water and the wet hair subjected to a longitudinal stress in the manner hereinabove described and allowed to dry. Hair treated in this manner is found to maintain its set even under conditions of high humidity.

As noted hereinabove, compounds of the formula $MHSO_5$ decompose relatively quickly on contact with water. In contrast, the dry monopersulfates are stable indefinitely. In order to provide the user of the shampoo compositions herein with a fresh solution of monopersulfate salt, it is necessary to package the shampoo and dry monopersulfate separately. In this way, the user can mix the ingredients just prior to application to the hair. Accordingly, the present invention encompasses hair deforming compositions in kit form, the kit comprising a separately packaged, aqueous shampoo composition and a separately packaged portion of a monopersulfate salt of the formula $MHSO_5$, wherein M is as defined above. The kit can contain sufficient shampoo and monopersulfate to provide multiple treatments, or can provide sufficient material for a single treatment. A kit suitable for single treatment use comprises from about 1.0 oz. to about 7.0 oz. of a separately packaged, water-based shampoo of the type hereinafter disclosed and from about 0.01 oz. to about 1.5 oz., preferably about 0.02 oz. to about 0.5 oz., of a separately packaged monopersulfate salt of the type disclosed herein. Kits of the foregoing size provide a sufficient volume of material for thorough saturation of the hair. Larger kits which are integral multiples of the single-use kits can be provided. With such multiple-use kits, it is convenient to provide a single, large volume of shampoo and incremental packets of monopersulfate salt. For use, an aliquot of shampoo is admixed with a single, premeasured package of the monopersulfate.

The kits herein are used by simply admixing the dry monopersulfate and the aqueous shampoo and agitating the mixture until the monopersulfate dissolves. The resulting solution is then applied to the hair, preferably hair which has been pre-moistened with water, in the manner disclosed above.

The shampoo compositions employed in the kits herein comprise water and a surfactant. The surfactant is, of course, an important ingredient in any shampoo composition, and the choice of surfactant for use in conjunction with the monopersulfate salts in the hair deforming kits herein is critical inasmuch as the cationic alkyl ammonium surfactants commonly employed in hair care compositions known in the art are not suitable for use in the shampoo compositions of this invention. As noted above, such positively charged materials apparently interact with the oxidized hair and interfere with its deformation. Accordingly, such cationic materials are preferably avoided in the shampoos herein. Other than the foregoing limitation, all manner of the well-known non-cationic, i.e., anionic, nonionic and amphoteric surfactants can be used in the shampoo-in hair setting composition herein.

Anionic surfactants such as the well-known, water-soluble salts of alkylbenzene sulfates and sulfonates wherein the alkyl group contains from about 10 to about 18 carbon atoms are useful in the shampoo compositions herein. Likewise, the water-soluble salts of fatty acids containing from about 10 to about 20 carbon atoms, i.e., soap, are suitable for use in monopersulfate shampoo compositions. Nonionic surfactants, such as the alkylated polyoxyethylenes, are useful in the shampoo compositions herein. Alkyl glycerol ether sulfates and sulfonates wherein the alkyl group contains from about 9 to about 21 carbon atoms are an especially preferred class of surfactants for use in the monopersulfate shampoo compositions. Amphoteric surfactants, such as the N-alkyl-sarcosinates having an alkyl group containing 9 to 20 carbon atoms are also useful herein. It is to be understood that the water-soluble salts of the foregoing anionic detergents, especially the alkali metal salts, are all useful as the surfactant component of the shampoo compositions herein.

Any of the foregoing types of surfactants are well known in the art and are commercially available. Especially preferred as the surfactant component of the monopersulfate shampoo compositions herein are the sodium alkyl glycerol ether sulfates, wherein the alkyl group contains from about 10 to about 18 carbon atoms; the sodium alkyl sulfates, wherein the alkyl group contains from about 10 to about 18 carbon atoms; sodium N-laurylsarcosinate, and mixtures thereof.

Shampoo compositions employed in the kits herein comprise from about 1% to about 20% by weight of a member selected from the group consisting of anionic, nonionic, and amphoteric surfactants, the balance of said compositions comprising water and minor portions of non-cationic cosmetic ingredients including anionic thickeners, perfumes, and the like, said shampoos having a pH within the range from about 5 to about 11, preferably from about 7 to about 9.5. As in the case of the curling and straightening compositions above, the shampoo compositions preferably contain from about 1% to about 20% by weight of a buffer capable of maintaining the pH within the selected basic range. Any of the pH buffer systems disclosed for use in the curling compositions herein are also suitable in the shampoos. The carbonate-bicarbonate buffer system is especially preferred in the shampoos herein. Accordingly, preferred shampoo compositions herein contain, as an additional component, from about 0.5% to about 10% by weight of sodium carbonate, and from about 0.5% to about 10% by weight of sodium bicarbonate, the total mixed carbonate-bicarbonate present in the composition being within the range of from about 1% to about 20% by weight of the total composition. The shampoo base is admixed with the monopersulfate salt to give freshly prepared shampoo-in composition for deforming hair containing at least about 1%, preferably 2% to 10%, by weight of the water-soluble monopersulfate salt.

The following examples are intended to illustrate hair styling kits comprising a shampoo and a monopersulfate salt and their use in deforming hair but are not intended to be limiting thereof.

EXAMPLE IV

| Component 1 | Amount |
|---|---|
| OXONE | 0.12 oz. |
| Component 2 | |
| Shampoo* | 4.0 oz. |

*Shampoo formulation comprising Sodium Alkyl Glycerol Ether Sulfate (Alkyl = mixed $C_{12}$–$C_{18}$) 1.8% by weight; Sodium Carbonate, 1.1% by weight; Sodium Bicarbonate, 5.3% by weight; Veegum, 2.8% by weight; Perfume, 0.65% by weight; Water, balance.

The full packet of OXONE is admixed with the full bottle of shampoo and agitated until all the OXONE dissolves. The pH of the composition is ca. 9.

The freshly prepared OXONE-shampoo composition of Example IV is used to curl hair as follows. The hair to be curled is first moistened with water and then all of the shampoo composition is applied to the hair and worked in until a lather forms. The composition is then allowed to remain in contact with the hair for 5 minutes, after which the hair is thoroughly rinsed with water and lightly towel dried. The moist hair is then wound in Croquignole manner using 1/4 in. mandrels and affixed in place at the scalp line. The hair is then allowed to dry at room temperature. After drying, the rollers are removed and the resulting hair is found to have a curl which is not readily removed under conditions of high relative humidity. The natural hair color is not affected by this treatment.

In the above composition, the packet of OXONE is replaced by 0.10 oz. packets of $LiHSO_5$, $NaHSO_5$, $RbHSO_5$, and $CsHSO_5$, respectively, and equivalent hair curling results are secured.

In the above kit, the carbonate-bicarbonate buffer system in the shampoo component is replaced by an equivalent amount of a sodium phosphate-sodium hydrogen phosphate buffer. The resulting shampoo composition has superior lipid removal properties. Hair treated with this shampoo in the foregoing manner maintains a curl even under conditions of high relative humidity.

In the above kit, the shampoo is prepared using deionized water. In addition, a 6 oz. bottle of deionized water is included in the kit. The deionized water is used to rinse the shampoo from the hair prior to setting.

EXAMPLE V

| Component 1 | Amount |
|---|---|
| OXONE | 0.45 oz. |
| Component 2 | |
| Shampoo* | 3.0 oz. |

*Shampoo formulation comprising Sodium Alkyl Sulfate (alkyl mixed $C_{12}$ – $C_{16}$),

EXAMPLE V-continued

| Component 1 | Amount |
|---|---|

1.0% by weight; Potassium Alkyl Glycerol Ether Sulfate (alkyl mixed $C_{12}$–$C_{18}$), 1% by weight; Sodium Carbonate, 1.1% by weight; Sodium Bicarbonate, 8% by weight; Sodium Carboxymethylcellulose, 3% by weight; Glycerol, 3% by weight; Perfume, 0.5% by weight; Water, balance.

The full packet of OXONE is admixed with the full bottle of shampoo and agitated until all the OXONE dissolves. The pH of the composition is ca. 8.5.

The freshly prepared OXONE-shampoo composition of Example V is used to straighten hair as follows. The hair to be straightened is first moistened with tap water and all of the shampoo composition is applied to the hair and worked in until a lather forms. The composition is then allowed to remain in contact with the hair for approximately 30 minutes, after which the hair is thoroughly rinsed with water and lightly towel dried. The moist hair is then combed into a substantially straight configuration and affixed in place with clips. The hair is then dried using a standard forced air dryer at a temperature of about 120°F. After drying, the clips are removed and the hair is in the substantially straight configuration. The straightened hair does not curl or kink under conditions of high relative humidity. The natural color of the hair is not substantially affected by this treatment.

In the above composition, the shampoo formulation is modified by replacing the sodium alkyl sulfate with an equivalent amount of sodium alkyl benzene sulfate (alkyl = 13.8 carbon atoms, avg.), sodium N-lauryl sarcosinate, sodium alkylglycerol sulfate (alkyl = $C_{10}$ – $C_{18}$) and sodium coconut soap, respectively, and equivalent results are secured.

The foregoing examples illustrate the hair deforming kits of the instant invention comprising a separately packaged, water-based, non-cationic shampoo and a separately packaged portion of a water-soluble monopersulfate oxidant, said portion being sufficient to provide a concentration of oxidant in the shampoo of at least about 1%, preferably about 1% to about 20% by weight. It is to be recognized that such compositions can contain other ingredients such as tints, emollients, hair control agents and the like, so long as such additional ingredients are not cationic in nature.

What is claimed is:

1. A hair deforming composition in kit form comprising: (1) a separately packaged, water-based shampoo; and, (2) a separately packaged portion of an oxidant of the formula $MHSO_5$, wherein M is an alkali metal cation, said portion being sufficient to provide a concentration of oxidant in the shampoo of at least about 1% by weight.

2. A kit according to claim 1 wherein the oxidant is $KHSO_5$.

3. A kit according to claim 1 wherein the shampoo contains a carbonate-bicarbonate buffer at a pH of from 7.0 to about 9.5.

4. A kit according to claim 1 which is designed for single use comprising: (1) from about 1.0 oz. to about 7.0 oz. of a separately packaged, water-based shampoo; and, (2) from about 0.01 oz. to about 1.5 oz. of the oxidant.

* * * * *